US00PP29629P3

(12) United States Plant Patent
Van Swieten

(10) Patent No.: US PP29,629 P3
(45) Date of Patent: Aug. 28, 2018

(54) ***PHALAENOPSIS* ORCHID PLANT NAMED 'PHALFNIWIN'**

(50) Latin Name: ***Phalaenopsis* hybrid**
Varietal Denomination: PHALFNIWIN

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 29 days.

(21) Appl. No.: 15/530,068

(22) Filed: Nov. 30, 2016

(65) Prior Publication Data

US 2018/0153075 P1 May 31, 2018

(51) Int. Cl.
*A01H 5/02* (2018.01)

(52) U.S. Cl.
USPC ..... Plt./311
CPC ..... *A01H 5/02* (2013.01)

(58) Field of Classification Search
USPC ..... Plt./311
See application file for complete search history.

*Primary Examiner* — Keith O. Robinson
(74) *Attorney, Agent, or Firm* — Jondle & Associates, P.C.

(57) ABSTRACT

A new and distinct variety of *Phalaenopsis* plant named 'PHALFNIWIN', particularly characterized by having large, light purple, spotted flowers (intensity and number of spots depend on the temperature), 1 to 2 peduncles that are long and sturdy, leaves that are obovate, and is propagated by meristem tissue culture, is disclosed.

3 Drawing Sheets

Genus and species: *Phalaenopsis* hybrid.
Variety denomination: 'PHALFNIWIN'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALFNIWIN'.

The new *Phalaenopsis* plant is a product of a planned breeding program conducted by the inventor in Bleiswijk, The Netherlands. The objective of this breeding program was to create a new *Phalaenopsis* plant with large, light purple, spotted flowers suitable for potted plant production. The intensity and number of spots depend on the temperature.

The new *Phalaenopsis* plant 'PHALFNIWIN' is a result of cross-pollination made by the inventor in October 2006 in Bleiswijk, The Netherlands of the proprietary female, or seed parent, *Phalaenopsis* hybrid '14261-01' (unpatented) with the proprietary male, or pollen parent, *Phalaenopsis* hybrid '01-1941' (unpatented).

The new *Phalaenopsis* was selected by the inventor as a single plant within the progeny of the stated cross-pollination in a controlled greenhouse in Bleiswijk, The Netherlands in October 2009. Asexual reproduction of the new *Phalaenopsis* plant by meristem tissue culture since 2012 in Bleiswijk, The Netherlands, has demonstrated that the new variety reproduces true to type with all of the characteristics, as herein described, firmly fixed and retained through successive generations.

Plant Breeder's Rights for this variety have been applied for in Europe on Sep. 13, 2016. 'PHALFNIWIN' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Bleiswijk, The Netherlands and can be used to distinguish 'PHALFNIWIN' as a new and distinct variety of *Phalaenopsis* plant.

1) Large, light purple, spotted flowers (intensity and number of spots depend on the temperature);
2) 1 to 2 peduncles;
3) Peduncle is long and sturdy; and
4) Shape of the leaf is obovate.

DESCRIPTION OF THE PHOTOGRAPHS

This new *Phalaenopsis* plant is illustrated by the accompanying photographs which show the overall plant habit including blooms and foliage of the plant; the colors shown are as true as can be reasonably obtained by conventional photographic procedures. The photographs were taken in a greenhouse in Bleiswijk, The Netherlands, from 50-week old plants in October 2016. Colors in the photographs may differ from the color values cited in the detailed botanical description, which accurately describe the actual colors of the new variety.

DESCRIPTION OF THE NEW VARIETY

Figure 1:
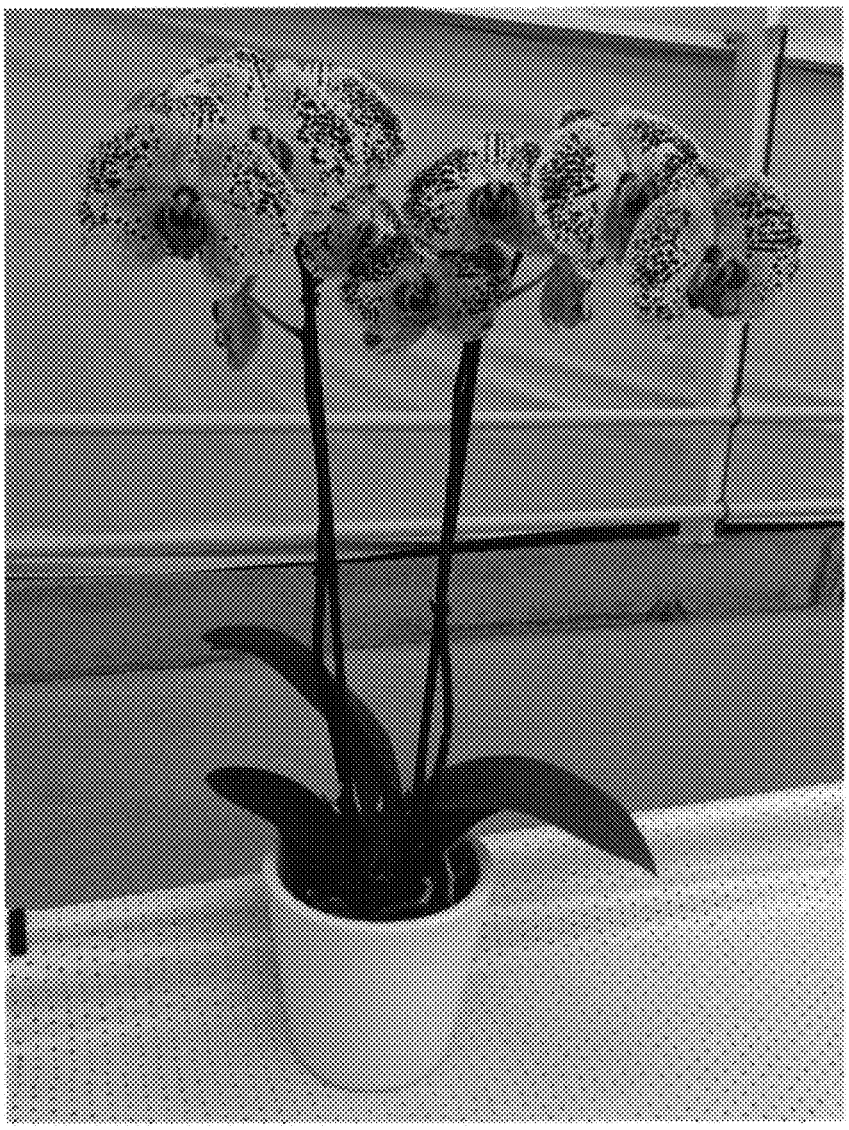
FIG. 1 shows the overall plant habit, including blooms and foliage of 'PHALFNIWIN'.
Figure 2:
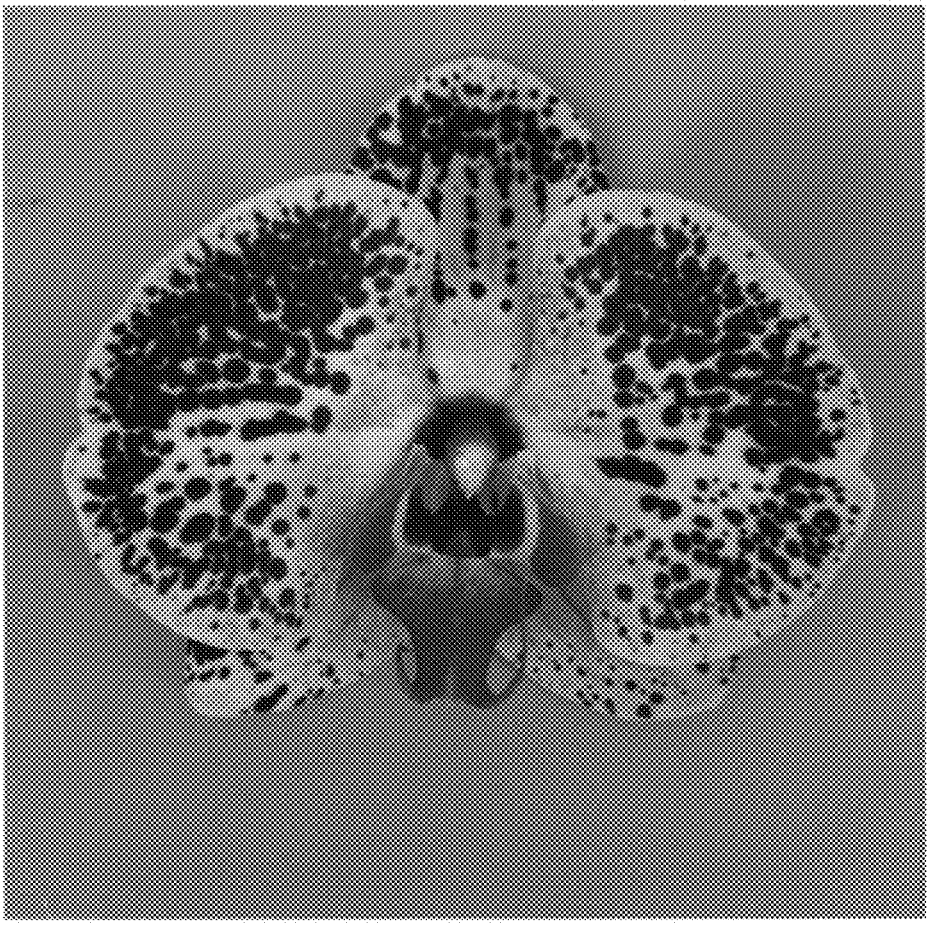
FIG. 2 shows a close-up of a flower of 'PHALFNIWIN'.
Figure 3:
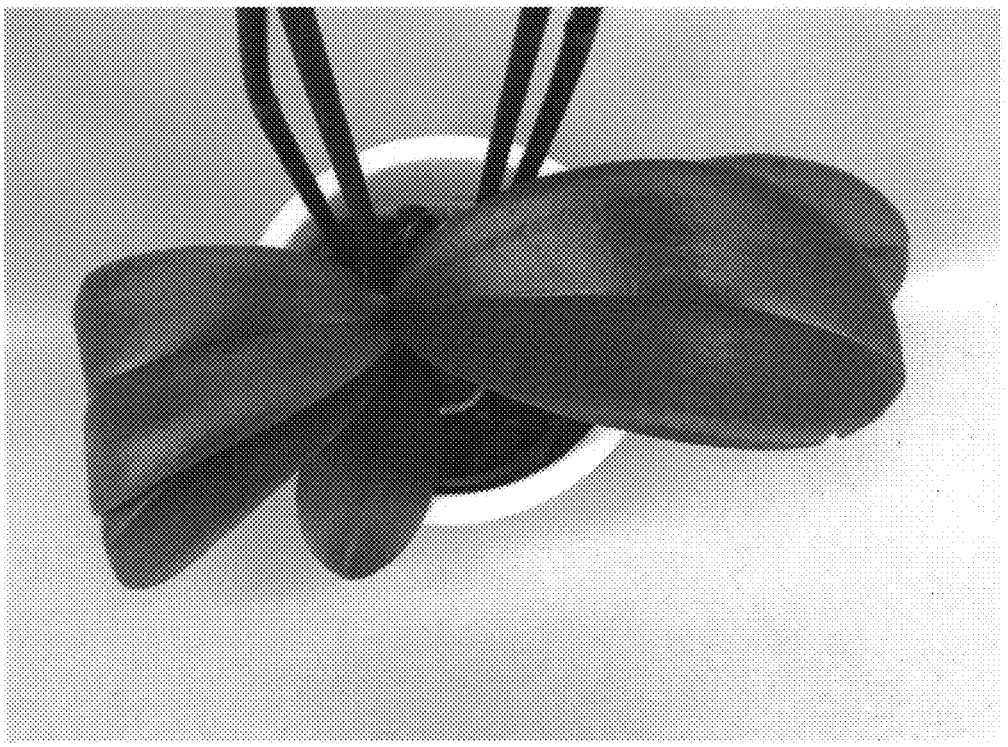
FIG. 3 shows a close-up of the leaves of 'PHALFNIWIN'.

The following detailed description sets forth the distinctive characteristics of 'PHALFNIWIN'. Plants of the new

*Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, The Netherlands. Observations and measurements were made in October 2016 on 50-week old plants which were planted from a nursery tray in 12 centimeter (diameter) pots and grown in a greenhouse between 27° C. to 29° C. for 30 weeks, continued by a cooling period of 8 weeks between 18° C. to 20° C. and 12 weeks in a greenhouse of 21° C.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALFNIWIN'.

Parentage:

*Female parent*.—*Phalaenopsis* cultivar '14261-01' (unpatented).

*Male parent*.—*Phalaenopsis* cultivar '01-1941' (unpatented).

Propagation:

*Type*.—Meristem tissue culture.

Roots:

*Root description*.—Greyed-green (RHS 190B/C) colored roots with green (RHS 146B/C) and diluting purple (RHS N77A) colored root tips. (The exact shades of the roots may vary with minimal changes of environmental conditions, such as root moisture or location inside or outside of the pot).

Plant:

*Commercial crop time to flowering*.—Approximately 48 to 50 weeks from a rooted cutting to finish in a 12 cm pot.

*Growth habit of peduncle*.—Standard, green leaves, raceme to panicle.

*Height* (*from soil level to top of inflorescence*).—Approximately 49.0 cm to 59.0 cm.

*Width* (*measured from leaf tips*).—About 35.0 cm to 40.0 cm.

*Vigor*.—Strong.

Leaves:

*Mature leaves*.—Quantity per plant: 7 to 9 leaves are produced before flowering. Length (fully expanded): 17.0 cm to 19.0 cm. Width: 7.0 cm to 7.5 cm. Shape: Oblong. Base shape: Moderately elongated. Apex: Unequal obtuse. Leaf blade angle with the petiole (measured from the horizontal position): Between 15 degrees and 30 degrees. Leaf margin: Entire. Color: Upper surface: RHS 146A. Lower surface: RHS 146B. Texture: Upper surface: A little bit rough. Lower surface: Smooth. Thickness: 2.1 mm to 2.3 mm. Variegation: Absent. Venation: Pattern: Parallel. Color of the midvein: Upper surface: RHS 146A. Lower surface: RHS 146B.

Peduncle:

*Quantity per plant*.—1 to 2.

*Number of flowers per peduncle*.—9 to 16.

*Length*.—44.0 cm to 54.0 cm.

*Diameter*.—5.4 mm to 5.7 mm.

*Strength*.—Strong.

*Aspect*.—Upright.

*Texture*.—Smooth.

*Color*.—Brown (RHS 200B) with a touch of green (RHS 146A).

*Internode length*.—40.0 mm to 50.0 mm.

*Callosities*.—None.

Inflorescence description:

*Appearance*.—Upright to slightly pendant, raceme to panicle inflorescence with bilaterally symmetrical flowers that open in succession beginning with the lowermost flower.

*Number of inflorescences*.—1 to 2.

*Inflorescence size*.—Height (from base to tip): 160.0 mm to 260.0 mm.

*Flowering time*.—First flowers can be expected 10 to 11 months after planting in a 12 cm (diameter) pot.

*Flower*.—Height: 85.0 mm to 90.0 mm. Diameter: 93.0 mm to 98.0 mm. Depth of lip: 24.0 mm to 26.0 mm.

*Flower longevity*.—On the plant: 10 to 14 weeks.

*Fragrance*.—Absent.

*Flower bud*.—Average size: Medium to large. Length: 24.0 mm to 26.0 mm. Width: 19.0 mm to 21.0 mm. Shape: Egg shaped. Color: Mix of light green (RHS 145B/C) and greyed-red (RHS 182B) with diluted purple spots (RHS N79A).

*Petals*.—Arrangement: Open/free. Shape: Semi-circular. Apex: Emarginated. Margin: Undulated. Length (from base to tip): 42.0 mm to 44.0 mm. Width: 58.0 mm to 60.0 mm. Position of broadest part of petal: Toward the base. Color (when fully opened): Upper surface: Basic color: Light purple (RHS 76D). Over color: Purple (RHS 187B) with dark purple spots (RHS N78C). Lower surface: Basic color: Light purple (RHS 76D). Over color: Purple (RHS 77D) and slightly light green (RHS 145D) at the base with diluted dark purple spots (RHS 187B).

*Dorsal sepal*.—Shape: Broad elliptic. Apex: Rounded to slightly emarginated. Margin: Entire. Length (from base to tip): 46.0 mm to 48.0 mm. Width: 34.0 mm to 36.0 mm. Color (when fully opened): Upper surface: Basic color: Light purple (RHS 76D). Over color: Purple (RHS N78C) with dark purple spots (RHS 187B). Lower surface: Basic color: Light purple (RHS 76C). Over color: Purple (RHS N78D) and light green (RHS 145C); with diluted dark purple spots (RHS 187B) at the edge.

*Lateral sepals*.—Shape: Ovate. Apex: Obtuse asymmetric. Margin: Entire. Length (from base to tip): 45.0 mm to 47.0 mm. Width: 30.0 mm to 32.0 mm. Color (when fully opened): Upper surface: Basic color: Light purple (RHS 76D) and light green (RHS 145C). Over color: Purple (RHS N78D) and light green (RHS 145C); with dark purple spots (RHS 187B). Lower surface: Basic color: Light purple (RHS 76D). Over color: Purple (RHS N78C) and light green (RHS 145C).

*Labellum* (*lip*).—Whiskers: Present. Length of whiskers: 14.0 mm to 16.0 mm. Color of whiskers: Red-purple (RHS 64A). Pubescence on the lip: Absent.

*Lateral lobe*.—Shape: Spatulate. Margin: Entire. Length (from base to tip): 19.0 mm to 21.0 mm. Width: 15.0 mm to 17.0 mm. Color: Red (RHS 185A) at the base; white (RHS 155C) and purple (RHS N78A) towards the edge; slightly yellow (RHS 7A) on one side.

*Apical lobe*.—Shape: Triangular. Margin: Entire. Length: 18.0 mm to 20.0 mm. Width: 20.0 mm to 22.0 mm. Color: Yellow (RHS 7A) at the base; purple (RHSA 64A) towards the whiskers.

*Callus*.—Average size: Medium to large. Height: 0.7 cm to 0.8 cm. Length: 0.6 cm to 0.7 cm. Width: 0.4 cm to 0.5 cm. Color: Dark purple (RHS 187A).

*Reproductive organs*.—Column: Length: 7.0 mm to 9.0 mm. Diameter: 5.4 mm to 5.6 mm. Color: Dark purple (RHS N79C) at the base and red-purple (RHS 72B). Pollinia: Quantity: 2. Diameter: 0.9 mm to 1.1 mm. Color: Orange (RHS 25A). Ovary: Length: 9.0 mm to 11.0 mm. Diameter: 2.6 mm to 2.8 mm. Pedicel: Length: 35.0 mm to 37.0 mm. Diameter: 3.0 mm to 3.2 mm. Color: Green (RHS 146D) at the base; light purple (RHS N75C/D) towards the flower.

Disease, pest, and stress resistance: No specific resistance or susceptibility observed to pathogens and pests common to *Phalaenopsis*.

Fruit and seeds: Fruit and seed development has not been observed on plants of the new *Phalaenopsis*.

COMPARISON WITH PARENTAL AND COMMERCIAL VARIETIES

'PHALFNIWIN' differs from female parent plant '14261-01' (unpatented) in that 'PHALFNIWIN' has a spotted flower pattern that is shaded in the center with a light purple center, whereas '14261-01' has an even flower pattern with a white center. Additionally, 'PHALFNIWIN' has shorter whiskers than '14261-01'.

'PHALFNIWIN' differs from male parent plant '01-1941' (unpatented) in that 'PHALFNIWIN' has a spotted flower pattern that is shaded in the center with a light purple center, whereas '01-1941' has a spotted flower pattern with a striped edge and a white center.

'PHALFNIWIN' is most similar to the commercial *Phalaenopsis* plants named 'PHALFOYX' (U.S. Plant Pat. No. 28,103) and 'PHALDUZAH' (U.S. Plant Pat. No. 26,830). 'PHALFNIWIN' differs from the commercial variety 'PHALFOYX' in that 'PHALFNIWIN' has a spotted flower pattern that is shaded in the center, an emarginated petal apex and an apical lobe that is yellow at the base and purple towards the whiskers, whereas 'PHALFOYX' has a spotted and edged flower pattern with the spots larger at the center and becoming smaller towards the edge, a rounded petal apex and a white apical lobe with yellow at the base and purple towards the whiskers and diluting dots. Additionally, 'PHALFNIWIN' has a spatulate lateral lobe, whereas 'PHALFOYX' has a weakly spatulate lateral lobe.

'PHALFNIWIN' differs from the commercial variety 'PHALDUZAH' in that 'PHALFNIWIN' has a spotted flower pattern that is shaded in the center and an apical lobe that is yellow at the base and dark purple towards the whiskers, whereas 'PHALDUZAH' has a flecked and centered flower pattern and an apical lobe that is yellow at the base with a stripe in the middle and light purple on both sides towards the whiskers.

I claim:

1. A new and distinct variety of *Phalaenopsis* plant named 'PHALFNIWIN', substantially as described and illustrated herein.

* * * * *